(12) United States Patent
Prakash et al.

(10) Patent No.: US 10,898,079 B2
(45) Date of Patent: Jan. 26, 2021

(54) INTRAVASCULAR PLAQUE DETECTION IN OCT IMAGES

(71) Applicant: University of Manitoba, Winnipeg (CA)

(72) Inventors: Ammu Prakash, Winnipeg (CA); Sherif S. Sherif, Winnipeg (CA)

(73) Assignee: University of Manitoba, Winnipeg (CA)

( * ) Notice: Subject to any disclaimer, the term of this patent is extended or adjusted under 35 U.S.C. 154(b) by 552 days.

(21) Appl. No.: 15/450,261

(22) Filed: Mar. 6, 2017

(65) Prior Publication Data
US 2017/0251931 A1 Sep. 7, 2017

Related U.S. Application Data

(60) Provisional application No. 62/303,767, filed on Mar. 4, 2016.

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0066* (2013.01); *A61B 5/0084* (2013.01); *A61B 5/6852* (2013.01); *A61B 5/6876* (2013.01); *A61B 5/7264* (2013.01); *G06K 9/00147* (2013.01); *G06K 9/622* (2013.01);
(Continued)

(58) Field of Classification Search
CPC ........................ G06T 2207/10101; G06T 7/40
See application file for complete search history.

(56) References Cited

U.S. PATENT DOCUMENTS

| | | | | |
|---|---|---|---|---|
| 5,644,232 A | * | 7/1997 | Smith .................... | G01R 33/56 324/304 |
| 7,260,248 B2 | * | 8/2007 | Kaufman ............. | A61B 5/0059 382/128 |

(Continued)

OTHER PUBLICATIONS

N Zayed, et al. "Statistical Analysis of Haralick Texture Features to Discriminate Lung Abnormalities", International Journal of Biomedical Imaging vol. 2015, p. 1-7 (Year: 2015).*

(Continued)

*Primary Examiner* — Gandhi Thirugnanam
(74) *Attorney, Agent, or Firm* — Adrian D. Battison; Ade & Company Inc; Michael R. Williams

(57) ABSTRACT

Detection of intravascular plaque in OCT images is carried out by obtaining images of vascular tissue from a vascular component by OCT either in a static mode of a single image or in a dynamic mode where the images are obtained by scanning. The method acts by dividing the OCT image into different regular regions, calculating different texture features for each of the above regions with a reduced set of less than a full set of the 26 Haralick textural features, using a clustering algorithm to segment the image defined by its texture features calculated above into different regions and transforming the segmented image back from its representation using texture features to its space-domain representation. The method uses three or four texture features where the reduced sets can be f1, f 2, and f14 (ASM at 0°, Inertia at 0° and ASM at 90°).

14 Claims, 5 Drawing Sheets

| Selected feature set | Feature name |
|---|---|
| $f1$ | Angular Second Moment at orientations(ASM) ($\theta = 0°$) |
| $f3$ | Inertia at orientations ($\theta = 0°$) |
| $f14$ | Angular Second Moment at orientations(ASM) ($\theta = 90°$) |

(51) Int. Cl.
| | |
|---|---|
| *G06T 7/00* | (2017.01) |
| *G06T 7/11* | (2017.01) |
| *G06T 7/40* | (2017.01) |
| *G06T 7/168* | (2017.01) |
| *G06K 9/62* | (2006.01) |
| *G06K 9/00* | (2006.01) |

(52) U.S. Cl.
CPC .............. *G06T 7/0012* (2013.01); *G06T 7/11* (2017.01); *G06T 7/168* (2017.01); *G06T 7/40* (2013.01); *A61B 2576/00* (2013.01); *G06T 2200/28* (2013.01); *G06T 2207/10101* (2013.01); *G06T 2207/30024* (2013.01); *G06T 2207/30101* (2013.01)

(56) References Cited

U.S. PATENT DOCUMENTS

| | | | | |
|---|---|---|---|---|
| 8,787,638 | B2* | 7/2014 | Zee | A61B 3/12 382/128 |
| 8,884,618 | B2* | 11/2014 | Mahfouz | A61F 2/3094 324/309 |
| 9,552,649 | B2* | 1/2017 | Banerjee | G06T 7/45 |
| 9,585,627 | B2* | 3/2017 | Liu | A61B 6/50 |
| 9,646,202 | B2* | 5/2017 | Abdollahian | G06K 9/68 |
| 10,004,471 | B2* | 6/2018 | Madabhushi | A61B 5/7267 |
| 2001/0031076 | A1* | 10/2001 | Campanini | G06K 9/3233 382/128 |
| 2003/0006770 | A1* | 1/2003 | Smith | F23C 6/045 324/309 |
| 2006/0039593 | A1* | 2/2006 | Sammak | G06K 9/00127 382/133 |
| 2006/0188158 | A1* | 8/2006 | Thiruvenkadam | G06T 7/12 382/171 |
| 2008/0118124 | A1* | 5/2008 | Madabhushi | G06K 9/469 382/128 |
| 2010/0138376 | A1* | 6/2010 | Avis | G06K 9/00986 706/50 |
| 2010/0177944 | A1* | 7/2010 | Madabhushi | G06K 9/6231 382/131 |
| 2010/0329529 | A1* | 12/2010 | Feldman | G06K 9/6252 382/131 |
| 2011/0026798 | A1* | 2/2011 | Madabhushi | G01R 33/56 382/131 |
| 2011/0026804 | A1* | 2/2011 | Jahanbin | G06K 9/52 382/141 |
| 2011/0103654 | A1* | 5/2011 | Lavoie | G06T 7/0012 382/128 |
| 2012/0243757 | A1* | 9/2012 | Funka-Lea | G06T 7/0002 382/131 |
| 2012/0316421 | A1* | 12/2012 | Kumar | A61B 1/00009 600/407 |
| 2013/0064441 | A1* | 3/2013 | Kask | G06K 9/00147 382/133 |
| 2013/0202173 | A1* | 8/2013 | Buckler | G06T 7/0012 382/131 |
| 2015/0100246 | A1* | 4/2015 | Remzi | G16H 50/30 702/19 |
| 2016/0143524 | A1* | 5/2016 | Berard | A61B 3/103 351/206 |
| 2016/0155225 | A1* | 6/2016 | Madabhushi | G06T 7/0012 382/131 |
| 2016/0171711 | A1* | 6/2016 | Gopinath | G06T 7/13 382/130 |
| 2017/0251931 | A1* | 9/2017 | Prakash | A61B 5/02007 |
| 2017/0270664 | A1* | 9/2017 | Hoogi | A61B 6/469 |
| 2017/0351939 | A1* | 12/2017 | Madabhushi | G01N 15/1475 |
| 2019/0087532 | A1* | 3/2019 | Madabhushi | G16Z 99/00 |
| 2019/0139219 | A1* | 5/2019 | Isgum | G06T 7/10 |

OTHER PUBLICATIONS

R. Haralick et al., "Textural Features for Image Classification", IEEE Transactions on systems, man and cybernetics, vol. SMC-3, No. 6, Nov. 1973, p. 610-621 (Year: 1973).*
A. Prakash et al., "Texture based segmentation method to detect atherosclerotic plaque from optical tomography images", European Conferences on Biomedical Optics, 2013, p. 1-7 (Year: 2013).*
Prakash A., Hewko M. D., Sowa M., et al., "Detection of Atherosclerotic Plaque From Optical Coherence Tomography Images Using Texture-Based Segmentation." Sovremennye Tehnologii. Papers 7(1), 21-28,(2015). (Year: 2015).*
Tom Weidong Cai, Jinman Kim, David Dagan Feng, "Content-Based Medical Image Retrieval",Biomedical Information Technology Biomedical Engineering, 2008, pp. 83-113 (Year: 2008).*
Vince DG1, Dixon KJ, Cothren RM, Cornhill JF.,"Comparison of texture analysis methods for the characterization of coronary plaques in intravascular ultrasound images.", Comput Med Imaging Graph. Jul.-Aug. 2000;24(4):221-229. (Year: 2000).*

* cited by examiner

| Feature Number | Feature name |
|---|---|
| f1, f14 | Angular Second Moment at orientations(ASM) ($\theta=0^0$, $\theta=90^0$) |
| f2, f15 | Correlation ($\theta=0^0$, $\theta=90^0$) |
| f3, f16 | Inertia at orientations ($\theta=0^0$, $\theta=90^0$) |
| f4, f17 | Variance at orientations ($\theta=0^0$, $\theta=90^0$) |
| f5, f18 | Inverse Difference Moment at orientations ($\theta=0^0$, $\theta=90^0$) |
| f6, f19 | Sum Average at angles ($\theta=0^0$, $\theta=90^0$) |
| f7, f20 | Sum Variance at orientations ($\theta=0^0$, $\theta=90^0$) |
| f8, f21 | Sum Entropy at orientations ($\theta=0^0$, $\theta=90^0$) |
| f9, f22 | Entropy at orientations ($\theta=0^0$, $\theta=90^0$) |
| f10, f23 | Difference Variance at orientations ($\theta=0^0$, $\theta=90^0$) |
| f11, f24 | Difference Entropy at orientations ($\theta=0^0$, $\theta=90^0$) |
| f12, f25 | Information Measure I of Correlation at orientations ($\theta=0^0$, $\theta=90^0$) |
| f13, f26 | Information Measure II of Correlation at orientations ($\theta=0^0$, $\theta=90^0$) |

FIG. 1A

| Selected feature set | Feature name |
|---|---|
| f1 | Angular Second Moment at orientations(ASM) ($\theta=0^0$) |
| f3 | Inertia at orientations ($\theta=0^0$) |
| f14 | Angular Second Moment at orientations(ASM) ($\theta=90^0$) |

FIG. 1B

INTRAVASCULAR PLAQUE DETECTION IN OCT IMAGES

This application claims the benefit under 35 USC 119 (e) of Provisional Application 62/303,767 filed Mar. 4, 2016.

This invention relates to a method of intravascular plaque detection in OCT images.

BACKGROUND OF THE INVENTION

Cardiovascular disease is one of the main causes of mortality and morbidity around the globe, and is expected to become the predominant cause of death worldwide [1]. Therefore, it is crucial for medical professionals to be able to detect the conditions that cause cardiovascular disease. The formation of vascular plaque is considered to be the underlying pathology of coronary heart disease as it can accumulate to the point where it blocks arterial blood flow. Many medical imaging methods have been utilized to detect vascular plaque, including: computed tomography (CT) [2-4], intravascular ultrasound (IVUS) [5-8], and magnetic resonance imaging (MRI) [9, 10]. OCT has been proven to be equally effective as high resolution IVUS in detecting calcified plaque morphologies, and there are several features that make it highly suitable for intravascular imaging. Among these features are high imaging resolution, the small size of the fiber-based imaging probes, and the availability of image processing techniques that allow physicians to extract diagnostic information from the resulting images. Studies have also shown that OCT has the ability to distinguish between different soft tissue structures by analyzing their textural properties [11]. Although segmentation of vascular has been carried out using IVUS [12], CT [13], and MRI [14], OCT has the unique ability of providing both micron scale morphological imaging with penetration depth (1 mm-3 mm).

In earlier work set out herein below, we proposed a method of automatically detecting vascular plaque by using full set of Haralick textural features and K-means clustering [15]. However, the computational complexity of our plaque detection method was limited by the dimensionality of the feature space. Therefore, it is very crucial to reduce the feature set by selecting only those features that characterize the vascular plaque texture. In this work, we identified a reduced set of 3 textural features that characterize vascular plaque in OCT images. Our new vascular plaque detection method solves the problem of redundancy and computational complexity, thus making it a viable option for handling real time applications. We also incorporated a new clustering technique (Fuzzy C-means) to detect plaque from this reduced feature space. One of the main advantages of Fuzzy C-means clustering over the standard K-means clustering is that it allows the data point to belong to more than one cluster by assigning a membership value. Thus, it is useful for overlapping data sets. Fuzzy C-means considers every data point to be a member of every cluster with varying degrees of membership. The previous work is explained in detail as follows:

Atherosclerosis as Cause of Cardiovascular Diseases

Cardiovascular diseases continue to be a leading cause of morbidity and mortality for both genders around the globe [1]. It is estimated that cardiovascular diseases are responsible for 30% of annual deaths in Canada. Therefore the ability to detect and diagnose conditions that could cause adverse cardiac events is very important. Atherosclerosis is considered to be the underlying cause of the majority of cardiovascular diseases [3]. Atherosclerosis is a process in which lipids such as cholesterol accumulate within the walls of arteries. A sequela of a series of immuno-inflammatory events in the arterial wall can lead to the development of atherosclerotic lesions. Plaques may appear with a wide range of morphological and anatomical features. Angiographic imaging methods are extremely good at finding flow-limiting stenotic lesions while computed tomography can accurately detect calcified lesions. The advent of intravascular ultrasound (IVUS) and intravascular OCT with their increased spatial resolution, enhanced contrast of soft tissues and volumetric imaging capability has lead to an interest in detecting and characterizing lesions. In particular, OCT with its very high resolution seems well suited to detect plaque risk stratification. Reliable detection of plaque with OCT and their prophylactic treatment at the time of intervention could potentially translate into an improved long term outcome for the patient.

Imaging of Plaque Using Optical Coherence Tomography

Optical coherence tomography (OCT) is analogous to ultrasound imaging which uses sound waves to create images with resolution of the order of tens of microns. OCT systems create images using back-reflection of infrared light instead of sound waves, which allows approximately 10 times higher imaging resolution than ultrasound at shallower penetration depths. The axial and lateral resolutions of OCT are approximately 5-10 µm and 15-30 µm, respectively.

Many biomedical imaging modalities have been utilized to detect plaque pathology. These modalities include intravascular ultrasound (IVUS) [4-7], computed tomography (CT) [8-10], and magnetic resonance imaging (MRI) [11, 12]. Intravascular optical coherence tomography (IVOCT) is a minimally invasive microscopic imaging technology that has been developed for the identification of plaque [13-16]. The first investigation of IVOCT demonstrated its potential to perform micron scale tomographic imaging of the internal microstructure of in vitro atherosclerotic plaques [17]. Several features of OCT make it attractive for intravascular imaging, e.g., high imaging resolution, small size of fiber-based imaging probes and the availability of image processing techniques to extract diagnostic information from the resulting images.

Studies have shown that using texture analysis, it may be possible for OCT to better distinguish different arterial structures in OCT images [18-23]. There exists literature on atherosclerotic plaque segmentation using Intravascular Ultrasound (IVUS) [24], computed tomography (CT) [25] and Magnetic resonance Imaging (MRI) [26]. However, OCT offers a combination of micron-scale morphological imaging with penetration depths of 1 mm-3 mm which makes it particularly attractive among other imaging modalities. A study was conducted comparing OCT-IVUS image pairs obtained from different patients [27, 28]. In all cases it was found IVOCT observations were more consistent than IVUS. On the basis of these findings, IVOCT has emerged as a promising imaging modality for extracting plaque diagnostic information.

Texture Segmentation of OCT Images

Texture segmentation is the process of identifying different regions within an image based on the different regions' texture. The properties of the texture of an image can be measured by its histogram and its statistical moments. There are different methods to extract texture features using statistical methods. There exists a large body of literature on texture feature extraction methods for example, Spatial Gray level dependent matrix (SGLDM) method, grey level difference method (GLDM), grey level run length method (GLRLM), and power spectral method (PSM) [29-31].

However a study comparing these methods has concluded that the SGLDM method is the most powerful texture feature extraction method [32]. Recent studies have shown that texture analysis can be useful in segmenting similar appearing tissue types based on its speckle features [33-35]

The following describes a method to segment regions of atherosclerotic plaque and vascular tissue on OCT images using SGLDM.

Experimental Setup

We used myocardial infarction prone Watanabe heritable hyperlipidemic rabbits, referred as WHHLMI rabbits [36, 37] to obtain samples of vascular tissues with atherosclerotic plaque. Arterial sample from two WHHLMI rabbits aged 10 months and 19 months at different locations were obtained. Arterial segments of tissue starting from the ascending aorta to the external iliac artery were excised from all specimens and subdivided into 20~30 mm long sections. This study was approved by the local animal care committee at Institute for Biodiagnostics, National Research Council Canada (Winnipeg, Manitoba).

OCT Imaging of Vascular Tissue Sample

We used a swept-source OCT (SS-OCT) system to image vascular tissue sample from WHHLMI rabbits The S-OCT system employed a central wavelength of 1310 nm with a sweep rate and spectral range of 30 khz and 110 nm respectively. Our SS-OCT unit was configured as a Mach-Zehnder interferometer with balanced optical detection.

Image Preprocessing

To achieve a uniform distribution of intensities and to improve contrast we performed image normalization on each raw OCT vascular image file. This was performed by a Min-Max normalization, defined as $$\text{Preprocessed\_Image} = \frac{\min(\text{Image})}{\max(\text{Image}) - \min(\text{Image})} \times 255 \quad (1)$$

To improve the image quality, we also performed image segmentation using automatic thresholding technique. Our raw OCT image contained 4 regions: air, plaque, vascular tissue and in-depth degraded signal, due to scattering. This segmentation method replaced the regions representing air with background, leaving the regions as background, region containing vascular tissue and plaque.

Feature Extraction and Feature Normalization

We extracted texture features from our processed OCT vascular images using SGLDM method. Features derived from the SGLDM method have been widely used for classification of tissue images [38-41]. The SGLDM method determines the probability of occurrence of specific grey levels as a function of pixel position in an image. This method makes use of co-occurrence or spatial dependence matrices which are texture transforms of the original image. These spatial dependence matrices are based on an estimate of second-order joint conditional probability density functions P (i, j; d, θ) [42-44]. These probability density functions, P (i, j; d, θ), measure the probability that two pixels, located at sample distance, d and direction, θ, have grey levels i and j. To detect the atherosclerotic plaque, we extracted 9 texture features in two directions with d=1 and θ=00 and 900 from these spatial dependence matrices directly. These SGLDM features are shown in Table 1. Even though these textural image features contain information about textural image characteristics of an image, it is difficult to identify which specific textural image characteristic is represented by each of these features [45]. However few of the features have visual definition for example F1 (Angular second moment) is the measure of smoothness of the image. The less smooth a region is, the lower its angular second moment. F8 (Entropy), is the measure of randomness in an image. For smooth images, the value of entropy will be low.

An important decision is to choose the size of the image window over which SGLDM matrices are calculated. Small windows may not have enough pixels to accurately capture the texture of underlying tissue while too large window may contain tissue of grossly different texture. We tried different window sizes and found the window size of 63×63 pixels led the best results for plaque segmentation from other regions.

The scale of the texture features has different dynamic ranges. To ensure that all the features have similar influence on performance of our method, we normalized the entire texture feature vector. Each texture feature vector was normalized as:

$$\hat{x} = \frac{x - \bar{x}}{\sigma} \quad (2)$$

where, x is the raw feature vector, $\bar{x}$ is the mean of all entries of x and σ is corresponding standard deviation.

Image Clustering Algorithm

After texture feature normalization, we carried out atherosclerotic plaque detection on OCT images using K-means clustering algorithm [46, 47, 48], which is a popular clustering technique due to its simplicity and fast convergence. We applied the K-means clustering algorithm on the texture feature space to segment the background, plaque, vascular tissue and in-depth degraded signal regions due to scattering and mapped the segmented features back to original image.

The K-means algorithm requires four parameters: (1) number of segments; (2) a distance metric (3) initial location of segments' centroids and (4) a criterion to stop iteration. As our preprocessed OCT images consist of background, plaque, vascular tissue, and in-depth degraded signal, we selected the number of segments, K=4. We defined distance between each segment by a Euclidean distance and initialized segment centroids randomly. For each texture feature vector, we calculated Euclidean distance from the segment centroid. Our criterion to stop iteration was, if the texture feature vector was not closest to its own segment centroid, it was to be shifted into the closest cluster. Otherwise, the feature vector was not shifted. The process continued until convergence was achieved.

Image Segmentation Results and Discussion

Our result shows different images of vascular tissue with segmented atherosclerotic plaque from a 10 month old WHHLMI rabbit and 19 month old WHHL rabbit. On comparing our segmented OCT with photographic image, it is clear that there exists a close match between the plaque locations. To the unaided eye, it will be difficult to differentiate the uniform appearing plaque and the remaining tissue regions from the raw OCT image.

K-means is considered as the standard unsupervised clustering method due to its simplicity and efficiency. The main goal of this algorithm is to partition data points into different clusters based on its similarities. It also requires user to specify the total number of clusters. In this work, we clustered data points based on its similar statistical properties from the OCT textural image. We assumed the total number of clusters which is 4 as prior information from the photographic vascular images. In future work, we aim to investigate different clustering algorithms which will not require the user to set a priori so as to improve the sensitivity. We also aim to reduce our number of features by employing feature reduction techniques and thereby extend our method to handle real time applications.

In the above work, we implemented an automated unsupervised clustering algorithm to detect the plaque region from OCT vascular images of arterial tissue in an automatic way. This approach mainly incorporates SGLDM method and K-means clustering algorithm. Our methodology extracts the texture features of the OCT vascular images based on their statistics rather than their visible structure. Our results show excellent matching with actual photographs of vascular tissue with atherosclerotic plaque. Our plaque detection approach is an important prerequisite to assess plaque vulnerability clinically. The ability of our method to detect invisible change in tissue structure could have significant impact to help diagnosis and management of atherosclerosis disease.

The following documents are relevant to the subject matter herein and may contain information of importance so that the disclosures are hereby incorporated by reference:

[1] A. M. Mimino, Deaths: Preliminary Data for 2008, DIANE Publishing, 2011.

[2] Statistics Canada. Morality, Summary List of Causes 2008. Released Oct. 18, 2011.

[3] M. Naghavi, et al. "From vulnerable plaque to vulnerable patient: a call for new definitions and risk assessment strategies: Part II," Circulation, vol. 108, no. 15, pp. 1772-1778, October 2003.

[4] G. J. Tearney and B. E. Bouma, "Atherosclerotic plaque characterization by spatial and temporal speckle pattern analysis," Opt. Lett., vol. 27, no. 7, pp. 533-535, April 2002.

[5] A. J. Martin, L. K. Ryan, A. I. Gotlieb, R. M. Henkelman, and F. S. Foster, "Arterial imaging: comparison of high-resolution US and MR imaging with histologic correlation," Radiographics, vol. 17, no. 1, pp. 189-202, February 1997.

[6] J. M. Tobis, J. Mallery, D. Mahon, K. Lehmann, P. Zalesky, J. Griffith, J. Gessert, M. Moriuchi, M. McRae, and M. L. Dwyer, "Intravascular ultrasound imaging of human coronary arteries in vivo. Analysis of tissue characterizations with comparison to in vitro histological specimens," Circulation, vol. 83, no. 3, pp. 913-926, March 1991.

[7] F. Prati, E. Arbustini, A. Labellarte, B. Dal, L. Sommariva, M. Mallus, A. Pagano, and A. Boccanelli, "Correlation between high frequency intravascular ultrasound and histomorphology in human coronary arteries," Heart, vol. 85, no. 5, pp. 567-570, May 2001.

[8] J. A. Rumberger, T. Behrenbeck, J. F. Breen, and P. F. Sheedy 2nd, "Coronary calcification by electron beam computed tomography and obstructive coronary artery disease: a model for costs and effectiveness of diagnosis as compared with conventional cardiac testing methods," J. Am. Coll. Cardiol., vol. 33, no. 2, pp. 453-462, February 1999.

[9] N. D. Wong, A. Vo, D. Abrahamson, J. M. Tobis, H. Eisenberg, and R. C. Detrano, "Detection of coronary artery calcium by ultrafast computed tomography and its relation to clinical evidence of coronary artery disease," Am. J. Cardiol., vol. 73, no. 4, pp. 223-227, February 1994.

[10] M. J. Budoff and B. H. Brundage, "Electron beam computed tomography: screening for coronary artery disease," Clin Cardiol, vol. 22, no. 9, pp. 554-558, September 1999.

[11] M. Naghavi, M. Madjid, M. R. Khan, R. M. Mohammadi, J. T. Willerson, and S. W. Casscells, "New developments in the detection of vulnerable plaque," Curr Atheroscler Rep, vol. 3, no. 2, pp. 125-135, March 2001.

[12] F. M. Baer, P. Theissen, C. A. Schneider, K. Kettering, E. Voth, U. Sechtem, and H. Schicha, "MRI assessment of myocardial viability: comparison with other imaging techniques," Rays, vol. 24, no. 1, pp. 96-108, March 1999.

[13] H. G. Bezerra, G. F. Attizzani, V. Sirbu, G. Musumeci, N. Lortkipanidze, Y. Fujino, W. Wang, S. Nakamura, A. Erglis, G. Guagliumi, and M. A. Costa, "Optical coherence tomography versus intravascular ultrasound to evaluate coronary artery disease and percutaneous coronary intervention," JACC Cardiovasc Interv, vol. 6, no. 3, pp. 228-236, March 2013.

[14] G. Parodi, A. Maehara, G. Giuliani, T. Kubo, G. S. Mintz, A. Migliorini, R. Valenti, N. Carrabba, and D. Antoniucci, "Optical coherence tomography in unprotected left main coronary artery stenting," EuroIntervention, vol. 6, no. 1, pp. 94-99, May 2010.

[15] N. Foin, J. M. Mari, J. E. Davies, C. Di Mario, and M. J. A. Girard, "Imaging of coronary artery plaques using contrast-enhanced optical coherence tomography," Eur Heart J Cardiovasc Imaging, vol. 14, no. 1, p. 85, January 2013.

[16] T. Wang, W. Wieser, G. Springeling, R. Beurskens, C. T. Lancee, T. Pfeiffer, A. F. W. van der Steen, R. Huber, and G. van Soest, "Intravascular optical coherence tomography imaging at 3200 frames per second," Opt. Lett., vol. 38, no. 10, pp. 1715-1717, May 2013.

[17] M. E. Brezinski, G. J. Tearney, B. E. Bouma, S. A. Boppart, M. R. Hee, E. A. Swanson, J. F. Southern, and J. G. Fujimoto, "Imaging of coronary artery microstructure (in vitro) with optical coherence tomography," The American Journal of Cardiology, vol. 77, no. 1, pp. 92-93, January 1996.

[18] K. W. Gossage, T. S. Tkaczyk, J. J. Rodriguez, and J. K. Barton, 'Texture analysis of optical coherence tomography images: feasibility for tissue classification', Journal of biomedical optics, vol. 8, no. 3, pp. 570-575, 2003

[19] A. A. Lindenmaier, L. Conroy, G. Farhat, R. S. DaCosta, C. Flueraru, and I. A. Vitkin, "Texture analysis of optical coherence tomography speckle for characterizing biological tissues in vivo," Opt. Lett., vol. 38, no. 8, pp. 1280-1282, April 2013.

[20] C. A. Lingley-Papadopoulos, M. H. Loew, M. J. Manyak, and J. M. Zara, "Computer recognition of cancer in the urinary bladder using optical coherence tomography and texture analysis," J Biomed Opt, vol. 13, no. 2, p. 024003, April 2008.

[21] M. Baroni, S. Diciotti, A. Evangelisti, P. Fortunato, and A. L. Torre, "Texture Classification of Retinal Layers in Optical Coherence Tomography," in 11th Mediterranean Conference on Medical and Biomedical Engineering and Computing 2007, T. Jarm, P. Kramar, and A. Zupanic, Eds. Springer Berlin Heidelberg, 2007, pp. 847-850.

[22] G. Quellec, K. Lee, M. Dolejsi, M. K. Garvin, M. D. Abràmoff, and M. Sonka, "Three-dimensional analysis of retinal layer texture: identification of fluid-filled regions in SD-OCT of the macula," IEEE Trans Med Imaging, vol. 29, no. 6, pp. 1321-1330, June 2010.

[23] M. Baroni, P. Fortunato, and A. La Torre, "Towards quantitative analysis of retinal features in optical coherence tomography," Medical Engineering & Physics, vol. 29, no. 4, pp. 432-441, May 2007.
[24] E. Brunenberg, O. Pujol, B. ter Haar Romeny, and P. Radeva, 'Automatic IVUS segmentation of atherosclerotic plaque with stop & go snake', Medical Image Computing and Computer-Assisted Intervention—MICCAI 2006, pp. 9-16, 2006.
[25] D. Vukadinovic, S. Rozie, M. van Gils, T. van Walsum, R. Manniesing, A. van der Lugt, and W. J. Niessen, 'Automated versus manual segmentation of atherosclerotic carotid plaque volume and components in CTA: associations with cardiovascular risk factors', Int J Cardiovasc Imaging, vol. 28, no. 4, pp. 877-887, April 2012.
[26] V. Amirbekian, M. J. Lipinski, K. C. Briley-Saebo, S. Amirbekian, J. G. S. Aguinaldo, D. B. Weinreb, E. Vucic, J. C. Frias, F. Hyafil, V. Mani, E. A. Fisher, and Z. A. Fayad, "Detecting and assessing macrophages in vivo to evaluate atherosclerosis noninvasively using molecular MRI," PNAS, vol. 104, no. 3, pp. 961-966, January 2007.
[27] B. D. MacNeill, H. C. Lowe, M. Takano, V. Fuster, and I. K. Jang, 'Intravascular Modalities for Detection of Vulnerable Plaque Current Status', Arteriosclerosis, thrombosis, and vascular biology, vol. 23, no. 8, pp. 1333-1342, 2003.
[28] I. K. Jang, B. E. Bouma, D. H. Kang, S. J. Park, S. W. Park, K. B. Seung, K. B. Choi, M. Shishkov, K. Schlendorf, and E. Pomerantsev, 'Visualization of coronary atherosclerotic plaques in patients using optical coherence tomography: comparison with intravascular ultrasound', Journal of the American College of Cardiology, vol. 39, no. 4, pp. 604-609, 2002.
[29] J. S. Weszka, C. R. Dyer, and A. Rosenfeld, 'A comparative study of texture measures for terrain classification', Systems, Man and Cybernetics, IEEE Transactions on, no. 4, pp. 269-285, 1976.
[30] M. M. Galloway, 'Texture analysis using gray level run lengths', Computer graphics and image processing, vol. 4, no. 2, pp. 172-179, 1975.
[31] G. G. Lendaris and G. L. Stanley, 'Diffraction-pattern sampling for automatic pattern recognition', Proceedings of the IEEE, vol. 58, no. 2, pp. 198-216, 1970.
[32] R. W. Conners and C. A. Harlow, 'A theoretical comparison of texture algorithms', Pattern Analysis and Machine Intelligence, IEEE Transactions on, no. 3, pp. 204-222, 1980.
[33] A. C. Sullivan, J. P. Hunt, and A. L. Oldenburg, "Fractal analysis for classification of breast carcinoma in optical coherence tomography," J. Biomed. Opt, vol. 16, no. 6, pp. 066010-066010-6, 2011.
[34] C. Flueraru, D. P. Popescu, Y. Mao, S. Chang, and M. G. Sowa, "Added soft tissue contrast using signal attenuation and the fractal dimension for optical coherence tomography images of porcine arterial tissue," Phys Med Biol, vol. 55, no. 8, pp. 2317-2331, April 2010.
[35] K. W. Gossage, C. M. Smith, E. M. Kanter, L. P. Hariri, A. L. Stone, J. J. Rodriguez, S. K. Williams, and J. K. Barton, "Texture analysis of speckle in optical coherence tomography images of tissue phantoms," Phys. Med. Biol., vol. 51, no. 6, p. 1563, March 2006.
[36] M. Shiomi, T. Ito, S. Yamada, S. Kawashima, and J. Fan, 'Development of an animal model for spontaneous myocardial infarction (WHHLMI rabbit)', Arteriosclerosis, thrombosis, and vascular biology, vol. 23, no. 7, pp. 1239-1244, 2003.
[37] T. Kobayashi, T. Ito, and M. Shiomi, "Roles of the WHHL Rabbit in Translational Research on Hypercholesterolemia and Cardiovascular Diseases," Journal of Biomedicine and Biotechnology, vol. 2011, pp. 1-10, 2011.
[38] C. I. Christodoulou, C. S. Pattichis, M. Pantziaris, and A. Nicolaides, 'Texture-based classification of atherosclerotic carotid plaques', Medical Imaging, IEEE Transactions on, vol. 22, no. 7, pp. 902-912, 2003.
[39] A. P. Dhawan, Y. Chitre, and C. Kaiser-Bonasso, 'Analysis of mammographic microcalcifications using gray-level image structure features', Medical Imaging, IEEE Transactions on, vol. 15, no. 3, pp. 246-259, 1996.
[40] C. M. Wu, Y. C. Chen, and K. S. Hsieh, 'Texture features for classification of ultrasonic liver images', Medical Imaging, IEEE Transactions on, vol. 11, no. 2, pp. 141-152, 1992.
[41] J. K. Kim and H. W. Park, 'Statistical textural features for detection of microcalcifications in digitized mammograms', Medical Imaging, IEEE Transactions on, vol. 18, no. 3, pp. 231-238, 1999.
[42] A. Nasser Esgiar, R. N. G. Naguib, B. S. Sharif, M. K. Bennett, and A. Murray, 'Microscopic image analysis for quantitative measurement and feature identification of normal and cancerous colonic mucosa', Information Technology in Biomedicine, IEEE Transactions on, vol. 2, no. 3, pp. 197-203, 1998.
[43] R. M. Haralick, K. Shanmugam, and I. H. Dinstein, 'Textural features for image classification', Systems, Man and Cybernetics, IEEE Transactions on, no. 6, pp. 610-621, 1973.
[44] F. Argenti, L. Alparone, and G. Benelli, 'Fast algorithms for texture analysis using co-occurrence matrices', in Radar and Signal Processing, IEE Proceedings F, 1990, vol. 137, pp. 443-448.
[45] B. Nielsen, F. Albregtsen, and H. E. Danielsen, 'Low dimensional adaptive texture feature vectors from class distance and class difference matrices', Medical Imaging, IEEE Transactions on, vol. 23, no. 1, pp. 73-84, 2004.
[46] J. A. Hartigan and M. A. Wong, 'Algorithm AS 136: A k-means clustering algorithm', Applied statistics, pp. 100-108, 1979.
[47] A. K. Jain, "Data clustering: 50 years beyond K-means," Pattern Recognition Letters, vol. 31, no. 8, pp. 651-666, June 2010.
[48] M. Kirby, A. M. Lee, T. Candido, C. MacAulay, P. Lane, S. Lam, and H. O. Coxson, "Automated segmentation of porcine airway wall layers using optical coherence tomography: comparison with manual segmentation and histology," 2014, vol. 8927, p. 89271D-89271D-9.

The following additional references include information relating to this field and are also incorporated herein by reference:

H. L. Graber, J. Chang, R. Aronson, and R. L. Barbour, "A perturbation model for imaging in dense scattering media: derivation and evaluation of imaging operators," Medical Optical Tomography: Functional Imaging and Monitoring, pp. 121-143, 1993.

V. V. Tuchin, Tissue Optics: Light Scattering Methods and Instruments for Medical Diagnosis. SPIE/International Society for Optical Engineering, 2007.

Z. Huang, H. Xu, A. D. Meyers, A. I. Musani, L. Wang, R. Tagg, A. B. Barqawi, and Y. K. Chen, 'Photodynamic therapy for treatment of solid tumors—potential and technical challenges', Technol Cancer Res Treat, vol. 7, no. 4, pp. 309-320, August 2008.

R. A. J. Groenhuis, H. A. Ferwerda, and J. J. Ten Bosch, "Scattering and absorption of turbid materials determined from reflection measurements. 1: Theory," Appl. Opt., vola 22, no. 16, pp. 2456-2462, August 1983.

A. N. Yaroslaysky, I. V. Yaroslaysky, T. Goldbach, and H.-J. Schwarzmaier, 'Optical properties of blood in the near-infrared spectral range', 1996, vol. 2678, pp. 314-324.

H. C. van de Hulst, Multiple Light Scattering. Tables, Formulas, and Applications. Volume 1. New York: Academic Pr, 1980.

S. R. Arridge, M. Cope, and D. T. Delpy, 'The theoretical basis for the determination of optical pathlengths in tissue: temporal and frequency analysis', Phys. Med. Biol., vol. 37, no. 7, p. 1531, July 1992.

A. H. Hielscher, J. R. Mourant, and I. J. Bigio, 'Influence of particle size and concentration on the diffuse backscattering of polarized light from tissue phantoms and biological cell suspensions', Appl Opt, vol. 36, no. 1, pp. 125-135, January 1997.

M. Kohl, M. Essenpreis, and M. Cope, 'The influence of glucose concentration upon the transport of light in tissue-simulating phantoms', Phys Med Biol, vol. 40, no. 7, pp. 1267-1287, July 1995.

W. C. Chew, Waves and Fields in Inhomogenous Media, New York: Wiley-IEEE Press, 1999.

M. Born, E. Wolf, A. B. Bhatia, P. C. Clemmow, D. Gabor, A. R. Stokes, A. M. Taylor, P. A. Wayman, and W. L. Wilcock, Principles of Optics: Electromagnetic Theory of Propagation, Interference and Diffraction of Light, 7 edition. Cambridge; New York: Cambridge University Press, 1999.

Ilker R. Çapoglu, J. D. Rogers, A. Taflove, and V. Backman, 'Accuracy of the Born approximation in calculating the scattering coefficient of biological continuous random media', Opt. Lett., vol. 34, no. 17, pp. 2679-2681, September 2009.

J. Ripoll, "Derivation of the scalar radiative transfer equation from energy conservation of Maxwell's equations in the far field.," JOSA A, vol. 28, no. 8, pp. 1765-1775, 2011.

J. Mobley and T. Vo-Dinh, "Optical Properties of Tissue," in Biomedical Photonics Handbook, CRC press Boca Raton, Fla., 2003.

J. M. Schmitt and A. Knüttel, "Model of optical coherence tomography of heterogeneous tissue," J. Opt. Soc. Am. A, vol. 14, no. 6, pp. 1231-1242, June 1997.

Z. Guo and S. Kumar, "Discrete-ordinates solution of short-pulsed laser transport in two-dimensional turbid media," Applied Optics, vol. 40, no. 19, pp. 3156-3163, 2001.

A. H. Hielscher, R. E. Alcouffe and R. L. Barbour, "Comparison of finite-difference transport and diffusion calculations for photon migration in homogeneous and heterogeneous tissues," Physics in Medicine and Biology, vol. 43, no. 5, pp. 1285-1302, 1998.

S. Arridge, M. Schweiger, M. Hiraoka and D. Delpy, "A finite element approach for modeling photon transport in tissue," Medical physics, vol. 20, no. 2, pp. 299-309, 1993.

D. O'Brien, "Accelerated quasi Monte Carlo integration of the radiative transfer equation," Journal of Quantitative Spectroscopy and Radiative Transfer, vol. 48, no. 1, pp. 41-59, 1992.

J. Fleck Jr and J. Cummings Jr, "An implicit Monte Carlo scheme for calculating time and frequency dependent nonlinear radiation transport," Journal of Computational Physics, vol. 8, no. 3, pp. 313-342, 1971.

L. Wang, S. L. Jacques and L. Zheng, "MCML—Monte Carlo modeling of light transport in multi-layered tissues," Elsevier, vol. 47, no. 2, pp. 131-146, 1995.

T. J. Pfefer, J. Kehiet Barton, E. K. Chan, M. G. Ducros, B. S. Sorg, T. E. Milner, J. S. Nelson and A. J. Welch, "A three-dimensional modular adaptable grid numerical model for light propagation during laser irradiation of skin tissue," IEEE Journal of Selected Topics in Quantum Electronics, vol. 2, no. 4, pp. 934-942, 1996.

T. Binzoni, T. Leung, R. Giust, D. Rufenacht and A. Gandjbakhche, "Light transport in tissue by 3D Monte Carlo: influence of boundary voxelization," Computer methods and programs in biomedicine, vol. 89, no. 1, pp. 14-23, 2008.

D. Boas, J. Culver, J. Stott and A. Dunn, "Three dimensional Monte Carlo code for photon migration through complex heterogeneous media including the adult human head," Optics express, vol. 10, no. 3, pp. 159-170, 2002.

T. Li, H. Gong and Q. Luo, "MCVM: Monte Carlo modeling of photon migration in voxelized media," Journal of Innovative Optical Health Sciences, vol. 3, no. 2, pp. 91-102, 2010.

H. Li, J. Tian, F. Zhu, W. Gong, L. V. Wang, E. A. Hoffman and G. Wang, "A mouse optical simulation environment (MOSE) to investigate bioluminescent phenomena in the living mouse with the monte carlo method," Academic Radiology, vol. 11, no. 9, pp. 1029-1038, 2004.

D. Cote and I. A. Vitkin, "Robust concentration determination of optically active molecules in turbid media with validated three-dimensional polarization sensitive Monte Carlo calculations," Optics express, vol. 3, no. 1, pp. 148-163, 2005.

E. Margallo-Balbs and P. J. French, "Shape based Monte Carlo code for light transport in complex heterogeneous tissues," Optics express, pp. 13086-14098, 2007.

N. Ren, J. Liang, X. Qu, J. Li, B. Lu and J. Tian, "CPU-based Monte Carlo simulation for light propagation in complex heterogeneous tissues.," Optics express, vol. 18, no. 7, pp. 6811-6823, 2010.

Q. Fang, "Mesh-based Monte Carlo method using fast ray-tracing in Plucker coordinates," Biomedical optics express, vol. 1, no. 1, pp. 165-175, 2010.

C. Zhu and Q. Liu, "Review of Monte Carlo modeling of light transport in tissues," Journal of biomedical optics, vol. 18, no. 5, pp. 050902-050902, 2013.

D. Huang, E. A. Swanson, C. P. Lin, J. S. Schuman, W. G. Stinson, W. Chang, M. R. Hee, T. Flotte, K. Gregory, C. A. Puliafito, and A. Et, "Optical coherence tomography," Science, vol. 254, no. 5035, pp. 1178-1181, November 1991.

A. F. Fercher, "Optical coherence tomography—development, principles, applications," Zeitschrift für Medizinische Physik, vol. 20, no. 4, pp. 251-276, November 2010.

W. Drexler and J. G. Fujimoto, Optical Coherence Tomography: Technology and Applications. Springer Science & Business Media, 2008.

D. Stifter, "Beyond biomedicine: a review of alternative applications and developments optical coherence tomography," Appl. Phys. B, vol. 88, no. 3, pp. 337-357, August 2007

S. S. Sherif, C. C. Rosa, C. Flueraru, S. Chang, Y. Mao, and A. G. Podoleanu, "Statistics of the depth-scan photocurrent in time-domain optical coherence tomography," J Opt Soc Am A Opt Image Sci Vis, vol. 25, no. 1, pp. 16-20, January 2008.

R. A. Leitgeb, R. M. Werkmeister, C. Blatter, and L. Schmetterer, "Doppler Optical Coherence Tomography," Progress in Retinal and Eye Research, vol. 41, pp. 26-43, July 2014.

Z. Chen, T. E. Milner, S. Srinivas, X. Wang, A. Malekafzali, M. J. C. van Gemert, and J. S. Nelson, "Noninvasive imaging of in vivo blood flow velocity using optical Doppler tomography," Opt. Lett., vol. 22, no. 14, pp. 1119-1121, July 1997.

Z. Chen and J. Zhang, "Doppler Optical Coherence Tomography," in Optical Coherence Tomography, P. D. W. Drexler and P. D. J. G. Fujimoto, Eds. Springer Berlin Heidelberg, 2008, pp. 621-651.

J. Moger, S. J. Matcher, C. P. Winlove, and A. Shore, "Measuring red blood cell flow dynamics in a glass capillary using Doppler optical coherence tomography and Doppler amplitude optical coherence tomography," J Biomed Opt, vol. 9, no. 5, pp. 982-994, October 2004.

Z. Chen, T. E. Milner, D. Dave, and J. S. Nelson, "Optical Doppler tomographic imaging of fluid flow velocity in highly scattering media," Opt. Lett., vol. 22, no. 1, pp. 64-66, January 1997.

R. A. Leitgeb, R. M. Werkmeister, C. Blatter, and L. Schmetterer, "Doppler Optical Coherence Tomography," Progress in Retinal and Eye Research, vol. 41, pp. 26-43, July 2014.

S. G. Proskurin, Y. He, and R. K. Wang, "Doppler optical coherence imaging of Converging flow," Phys Med Biol, vol. 49, no. 7, pp. 1265-1276, April 2004.

S. G. Proskurin, I. A. Sokolova, and R. K. Wang, "Imaging of non-parabolic velocity Profiles in converging flow with optical coherence tomography," Phys. Med. Biol., vol. 48, no. 17, p. 2907, September 2003.

B. Saleh, Introduction to Subsurface Imaging. Cambridge; New York: Cambridge University Press, 2011

Y. Zhao, Z. Chen, C. Saxer, S. Xiang, J. F. de Boer, and J. S. Nelson, "Phase-resolved optical coherence tomography and optical Doppler tomography for imaging blood flow in human skin with fast scanning speed and high velocity sensitivity," Opt. Lett., vol. 25, no. 2, pp. 114-116, January 2000.

Y. Zhao, Z. Chen, C. Saxer, Q. Shen, S. Xiang, J. F. de Boer, and J. S. Nelson, "Doppler standard deviation imaging for clinical monitoring of in vivo human skin blood flow," Opt. Lett., vol. 25, no. 18, pp. 1358-1360, September 2000.

M. J. Yadlowsky, J. M. Schmitt, and R. F. Bonner, "Multiple scattering in optical coherence microscopy," Appl. Opt., vol. 34, no. 25, pp. 5699-5707, September 1995.

J. M. Schmitt, A. Knuttel, M. Yadlowsky, and M. A. Eckhaus, "Optical-coherence tomography of a dense tissue: statistics of attenuation and backscattering," Phys. Med. Biol., vol. 39, no. 10, p. 1705, October 1994.

J. M. Schmitt, A. Knuttel, and R. F. Bonner, "Measurement of optical properties of biological tissues by low-coherence reflectometry," Appl. Opt., vol. 32, no. 30, pp. 6032-6042, October 1993.

M. Schmitt, M. J. Yadlowsky, and R. F. Bonner, "Subsurface imaging of living skin with optical coherence microscopy," Dermatology (Basel), vol. 191, no. 2, pp. 93-98, 1995.

M. J. Yadlowsky, J. M. Schmitt, and R. F. Bonner, "Contrast and resolution in the optical-coherence microscopy of dense biological tissue," 1995, vol. 2387, pp. 193-203.

Y. Pan, R. Birngruber, and R. Engelhardt, "Contrast limits of coherence-gated imaging in scattering media," Appl. Opt., vol. 36, no. 13, pp. 2979-2983, May 1997.

J. M. Schmitt and A. Knuttel, "Model of optical coherence tomography of heterogeneous tissue," J. Opt. Soc. Am. A, vol. 14, no. 6, pp. 1231-1242, June 1997.

D. J. Smithies, T. Lindmo, Z. Chen, J. S. Nelson, and T. E. Milner, "Signal attenuation and localization in optical coherence tomography studied by Monte Carlo simulation," Phys Med Biol, vol. 43, no. 10, pp. 3025-3044, October 1998.

G. Yao and L. V. Wang, "Monte Carlo simulation of an optical coherence tomography signal in homogeneous turbid media," Phys Med Biol, vol. 44, no. 9, pp. 2307-2320, September 1999.

A. Tycho, T. M. Jorgensen, H. T. Yura and P. E. Andersen, "Derivation of a Monte Carlo method for modeling heterodyne detection in optical coherence tomography systems," Applied optics, vol. 41, no. 31, pp. 6676-6691, 2002.

R. K. Wang, "Signal degradation by multiple scattering in optical coherence tomography of dense tissue: a Monte Carlo study towards optical clearing of biotissues," Physics in medicine and biology, vol. 47, no. 13, p. 2281-2299, 2002.

M. Y. Kirillin, A. V. Priezzhev, J. Hast and R. Myllyla, "Monte Carlo simulation of optical clearing of paper in optical coherence tomography," Quantum Electron, vol. 36, no. 2, pp. 174-180, 2006.

I. T. Lima, A. Kalra, and S. S. Sherif, "Improved importance sampling for Monte Carlo simulation of time-domain optical coherence tomography," Biomed Opt Express, vol. 2, no. 5, pp. 1069-1081, 2011.

I. T. Lima, A. Kalra, H. E. Hernandez-Figueroa, and S. S. Sherif, "Fast calculation of multipath diffusive reflectance in optical coherence tomography," Biomed Opt Express, vol. 3, no. 4, pp. 692-700, March 2012.

M. Y. Kirillin, E. Alarousu, T. Fabritius, R. Myllyla and A. V. Priezzhev, "Visualization of paper structure by optical coherence tomography: Monte Carlo simulations and experimental study," Journal of the European Optical Society-Rapid publications, vol. 2, p. 07031, 2007.

S. Malektaji, I. T. Lima, and S. S. Sherif, "Monte Carlo simulation of optical coherence tomography for turbid media with arbitrary spatial distributions," J Biomed Opt, vol. 19, no. 4, p. 046001, April 2014.

S. Malektaji, I. Lima, and S. S. Sherif, "Simulation of optical coherence tomography imaging of an arbitrary shaped turbid object," in Biomedical Optics 2014, 2014, p. BT3A.69.

M. R. Escobar I., S. Malektaji, I. T. Lima, and S. S. Sherif, "Accelerated simulation of optical coherence tomography of objects with arbitrary spatial distributions," 2014, p. 928818.

Kalkman, A. V. Bykov, D. J. Faber, and T. G. van Leeuwen, "Multiple and dependent scattering effects in Doppler optical coherence tomography," Opt. Express, vol. 18, no. 4, pp. 3883-3892, February 2010.

J. Kalkman, A. V. Bykov, G. J. Streekstra, and T. G. van Leeuwen, "Multiple scattering effects in Doppler optical coherence tomography of flowing blood," Phys Med Biol, vol. 57, no. 7, pp. 1907-1917, April 2012.

G. B. Chapman, "Review of Confocal Microscopy by T. Wilson," Transactions of the American Microscopical Society, vol. 110, no. 2, pp. 194-196, April 1991.

I. J. Cox and C. J. R. Sheppard, 'Information capacity and resolution in an optical system', J. Opt. Soc. Am. A, vol. 3, no. 8, pp. 1152-1158, August 1986.

C. J. R. Sheppard, C. J. Cogswell, and M. Gu, 'Signal strength and noise in confocal microscopy: Factors influencing selection of an optimum detector aperture', Scanning, vol. 13, no. 3, pp. 233-240, January 1991.

C. J. R. Sheppard, 'Stray light and noise in confocal microscopy', Micron and Microscopica Acta, vol. 22, no. 3, pp. 239-243, 1991.

E. A. Swanson, J. A. Izatt, C. P. Lin, J. G. Fujimoto, J. S. Schuman, M. R. Hee, D. Huang, and C. A. Puliafito, 'In vivo retinal imaging by optical coherence tomography', Opt. Lett, vol. 18, no. 21, pp. 1864-1866, November 1993.

J. M. Schmitt, A. Knüttel, and M. Yadlowsky, 'Confocal microscopy in turbid media', J. Opt. Soc. Am. A, vol. 11, no. 8, pp. 2226-2235, August 1994.

M. Kempe, E. Welsch, and W. Rudolph, 'Comparative study of confocal and heterodyne microscopy for imaging through scattering media', J. Opt. Soc. Am. A, vol. 13, no. 1, pp. 46-52, January 1996

C. J. R. Sheppard, S. S. Kou, and C. Depeursinge, 'Reconstruction in interferometric synthetic aperture microscopy: comparison with optical coherence tomography and digital holographic microscopy', J. Opt. Soc. Am. A, vol. 29, no. 3, pp. 244-250, March 2012.

J. M. Schmitt, A. R. Knuettel, A. H. Gandjbakhche, and R. F. Bonner, "Optical characterization of dense tissues using low-coherence interferometry," 1993, vol. 1889, pp. 197-211.

R. F. Lutomirski and H. T. Yura, "Propagation of a Finite Optical Beam in an Inhomogeneous Medium," Appl. Opt., vol. 10, no. 7, pp. 1652-1658, July 1971.

Y. Pan, R. Birngruber, J. Rosperich, and R. Engelhardt, "Low-coherence optical tomography in turbid tissue: theoretical analysis," Appl. Opt., vol. 34, no. 28, pp. 6564-6574, October 1995.

L. Thrane, H. T. Yura, and P. E. Andersen, "Optical coherence tomography: new analytical model and the shower curtain effect," 2000, vol. 4001, pp. 202-208

L. Thrane, H. T. Yura, and P. E. Andersen, "Calculation of the maximum obtainable probing depth of optical coherence tomography in tissue," 2000, vol. 3915, pp. 2-11.

A. Tycho, T. M. Joergensen, and L. Thrane, "Focusing problem in OCT: comparison of Monte-Carlo simulations, the extended Huygens-Fresnel principle, and experiments," 2000, vol. 3915, pp. 25-35.

P. E. Andersen, L. Thrane, H. T. Yura, A. Tycho, and T. M. Joergensen, "Modeling the optical coherence tomography geometry using the extended Huygens-Fresnel principle and Monte Carlo simulations," 2000, vol. 3914, pp. 394-406.

L. Thrane, H. T. Yura, and P. E. Andersen, "Analysis of optical coherence tomography systems based on the extended Huygens Fresnel principle," J. Opt. Soc. Am. A, vol. 17, no. 3, pp. 484-490, March 2000

H. T. Yura, "Signal-to-Noise Ratio of Heterodyne Lidar Systems in the Presence of Atmospheric Turbulence," in Surveillance of Environmental Pollution and Resources by Electromagnetic Waves, T. Lund, Ed. Springer Netherlands, 1978, pp. 67-93.

I. Dror, A. Sandrov, and N. S. Kopeika, "Experimental investigation of the influence of the relative position of the scattering layer on image quality: the shower curtain effect," Appl. Opt., vol. 37, no. 27, pp. 6495-6499, September 1998.

J. C. I. Bruno, "One-dimensional inverse scattering problem for optical coherence tomography," 2005

T. Fukano and I. Yamaguchi, "Simultaneous measurement of thicknesses and refractive indices of multiple layers by a low-coherence confocal interference microscope," Opt. Lett., vol. 21, no. 23, pp. 1942-1944, December 1996.

T. Fukano and I. Yamaguchi, "Separation of measurement of the refractive index and the geometrical thickness by use of a wavelength-scanning interferometer with a confocal microscope," Appl. Opt., vol. 38, no. 19, pp. 4065-4073, July 1999

G. J. Tearney, M. E. Brezinski, B. E. Bouma, M. R. Hee, J. F. Southern, and J. G. Fujimoto, "Determination of the refractive index of highly scattering human tissue by optical coherence tomography," Opt. Lett., vol. 20, no. 21, pp. 2258-2260, November 1995

J. W. Goodman, Statistical Optics, 1 edition. New York: Wiley-Interscience, 2000.

SUMMARY OF THE INVENTION

It is an object of the present invention to provide an improved method to automatically detect vascular plaque regions from OCT images.

According to the invention there is provided a method for detection of intravascular plaque in OCT images comprising:

obtaining at least one image of vascular tissue from a vascular component by OCT;

dividing the OCT image into different regular regions;

calculating different texture features for each of the above regions with a reduced set of less than a full set of the 26 Flaralick textural features;

using a clustering algorithm to segment the image as now defined by its texture features calculated above into different regions.

Preferably the method uses reduced set of features for example f1, f 2, and f14 (ASM at 0°, Inertia at 0° and ASM at 90°) out of a full set of 26 textural features.

Preferably the method includes the step of transforming the segmented image back from its representation using texture features to its space-domain representation.

In the preferred method, the clustering algorithm comprises Fuzzy C-means. However other clustering algorithm are available including K-means.

Preferably the reduction of the full set of the 26 Haralick textural features to a reduced set of three or four textural features is obtained by using a genetic algorithm optimization method, many other optimization technique can also be used.

Preferably the reduced number of features is selected and arranged so as to decrease the computation time without losing any textural information.

Preferably the method includes paralleling the algorithms for the reduced number of features so that they are calculated in parallel rather than sequentially so as to further decrease the computation time, such as by using a CUDA machine.

Preferably the reduced number of features is selected and arranged so as to reduce the computation time by more than four times.

While the method herein can be used for static images, preferably the reduced number of features is selected and arranged for use in real time applications of intravascular plaque detection using OCT images where there is provided a presentation to a technician of a real time image of the plaque detection as the vascular component is scanned using the apparatus.

For example the OCT images can typically be obtained by an optical fiber which is pulled through the vascular component.

In this case the vascular plaque from the OCT images is detected from a sequence of overlapping images obtained by moving an OCT probe over underlying tissue.

Preferably in this case the step size with which the OCT probe moves over the tissue is small compared to the probe's field of view so that each obtained image has many pixels in common with a previous image.

Since the clustering algorithm is recursive in nature, it therefore preferably acts to segment region pixels defined by texture features by assigning them to different image segments over and over again until a steady state solution is reached.

In this way removal and addition of a relatively small number of region pixels only slightly perturbs the steady state solution obtained by the clustering algorithm so that the previous steady state solution acts as a start solution to segment the next image.

More generally, optical coherence tomography (OCT) images are capable of detecting vascular plaque by using the full set of 26 Haralick textural features and the standard K-means clustering algorithm. However, the use of the full set of 26 textural features is computationally expensive and may not be feasible for real time implementation. Also, standard K-means clustering algorithm have few limitations such as it does not work very well with overlapping data sets and it is also sensitive to outliers. The purpose of this work is to overcome these limitations. In this work, we identified a reduced set of 3 textural feature which characterizes vascular plaque and used a generalized Fuzzy C-means clustering algorithm. Our work involves three steps: (ii) the reduction of a full set 26 textural feature to a reduced set of 3 textural features by using genetic algorithm (GA) optimization method (iii) the implementation of an unsupervised generalized clustering algorithm (Fuzzy C-means) on the reduced feature space, and (iii) the validation of our results using histology and actual photographic images of vascular plaque. Our results show an excellent match with histology and actual photographic vascular tissue images. Therefore, our results could provide an efficient clinical tool for the detection of vascular plaque in real time OCT imaging.

The present invention is applicable to OCT techniques using any of the imaging methods available to a person skilled in this art.

The present invention provides a method which also uses an advanced clustering technique. Our plaque detection method with three features dramatically decreases the computation time without losing any textural information.

Therefore the method can provide an efficient tool in real time applications of intravascular plaque detection using OCT images.

Preferably the method includes paralleling the algorithms for the reduced number, for example three features so that they are calculated in parallel rather than sequentially. This acts to further decrease the computation time. This can be done using a CUDA machine.

This method that detects vascular plaque using only for example three features can reduce the computation time by more than four times.

In this invention, we have presented an innovative method for using OCT images to characterize vascular tissue texture with a reduced set of three textural features.

The method can also be used to combines the genetic algorithm optimization with an advanced clustering technique (Fuzzy C-means) in order to detect vascular plaque in OCT images. Since the class labels (non-plaque and plaque) were not known in priori, we used the unsupervised approach.

We successfully reduced the number of features from the full set of 26 textural features to a reduced set of for example three textural features, and we quantitatively evaluated the accuracy of our method by comparing our plaque detection results with both the 26 texture feature set and the three feature set (see table 3). We used our segmentation result with full set of 26 textural features as the standard to calculate the error for reduced set of three textural features. The segmentation error was calculated by comparing the segmented plaque regions in the reduced set of three textural features with full set of 26 textural features.

The new reduced feature sets, which may for example be selected are f1, f2, and f14 (ASM at 0°, Inertia at 0° and ASM at 90°), along with Fuzzy C-means clustering, will help to characterize vascular plaque using OCT images. However other feature sets may be selected and the number may be more than three, provided the number if reduced.

Preferably the number is reduced and the calculations carried out sufficiently quickly to allow the presentation to the technician of a real time image of the plaque detection as the vascular component is scanned using the apparatus, typically an optical fiber which is pulled through the vascular component.

The time comparison results show that our algorithm becomes more than 5 times faster when the set of features is reduced. We also profiled the computation time in order to analyze the processing time in each step of our algorithm. We observed that more than 90% of the processing time is spent on feature calculation. Therefore, the method can include an arrangement to parallelize our algorithm by using GPU based CUDA machine to further reduce the processing time and to implement in real time applications.

The method herein thus implements an unsupervised clustering algorithm to detect vascular plaque from OCT images by using a reduced set of three textural features. The work mainly incorporates identifying a reduced set of, for example, three textural features from the full set of 26 textural features and implementing Fuzzy C-means algorithm. We validated our plaque detection results using both histology and photographic images. We also compared our results with those using a complete 26 feature set to show the robustness of using a 3 feature set. Our proposed method offers an efficient prerequisite to detect vascular clinically in real time basis. To our knowledge, this is the first automatic technique that detects vascular plaque through OCT images using a reduced set 3 textural features and the Fuzzy C-means clustering algorithm.

BRIEF DESCRIPTION OF THE DRAWINGS

One embodiment of the invention will now be described in conjunction with the accompanying drawings in which:

FIG. 1A is a table 1 where there is shown all of the Haralick textural features in 0 degrees and 90 degrees with d=1.

FIG. 1B is a table 2 which is a list of the selected Haralick texture features set in 0 degrees and 90 degrees with d=1.

DETAILED DESCRIPTION

Figure 1:
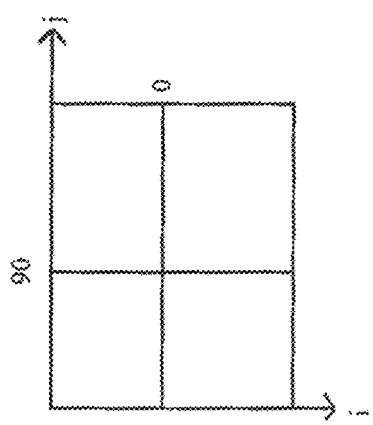
FIG. 1 shows the two (0° and 90°) orientations used to construct SGLDM matrices in our algorithm.
Figure 2A:
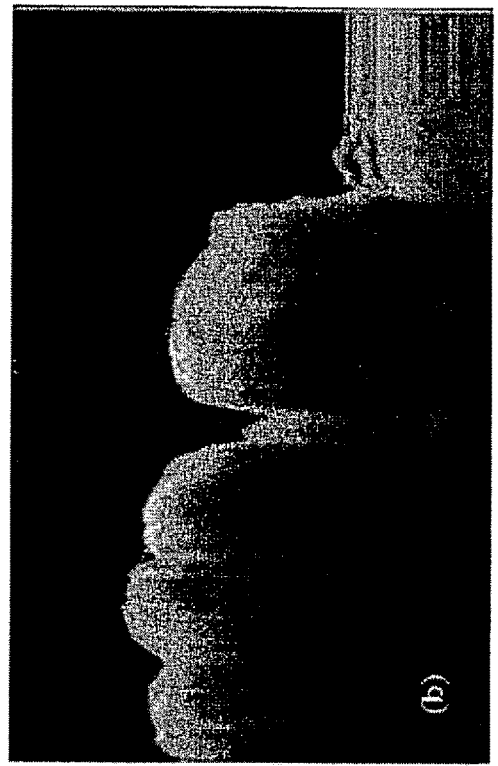
FIG. 2(a) shows a photographic OCT image at the marked B-scan location relating to the vascular tissue of a 22 month old WHHL rabbit.
Figure 2B:
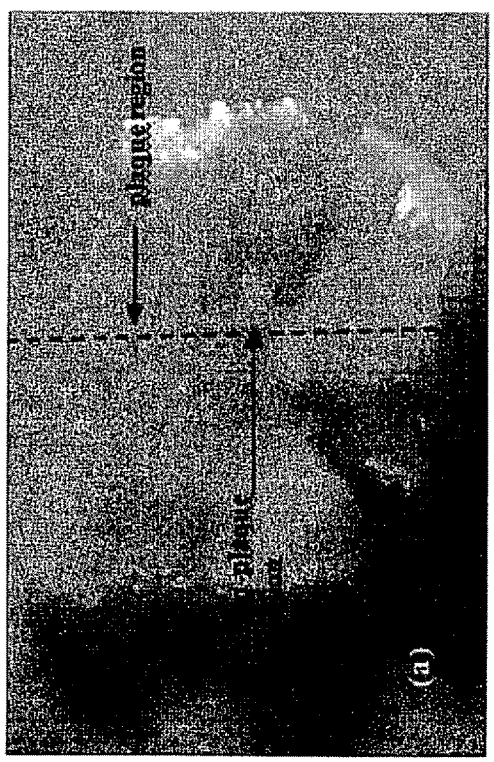
FIG. 2(b) shows a raw OCT image at the marked B-scan location relating to the vascular tissue of a 22 month old WHHL rabbit.
Figure 2E:
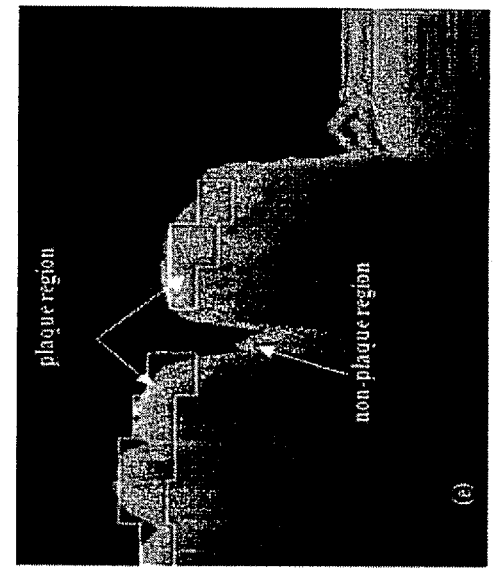
FIG. 2(e) shows the plaque detection results shown on the OCT image with reduced set of 3 textural features relating to the vascular tissue of a 22 month old WHHL rabbit.
Figure 2D:
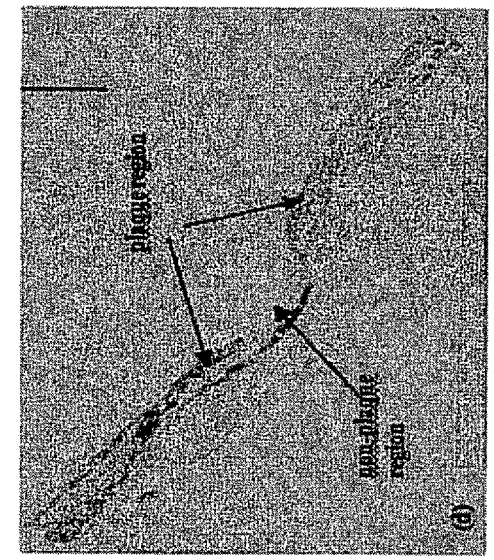
FIG. 2(c) shows plaque detection results as shown on the OCT image with full set of 26 textural features relating to the vascular tissue of a 22 month old WHHL rabbit.
FIG. 2 (d) shows the oil red histology image of vascular tissue depicting both plaque and non plaque regions relating to the vascular tissue of a 22 month old WHHL rabbit.
Figure 2C:
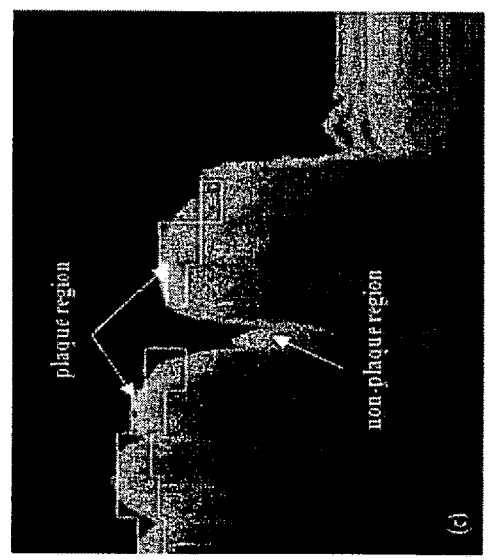
Figure 3A:
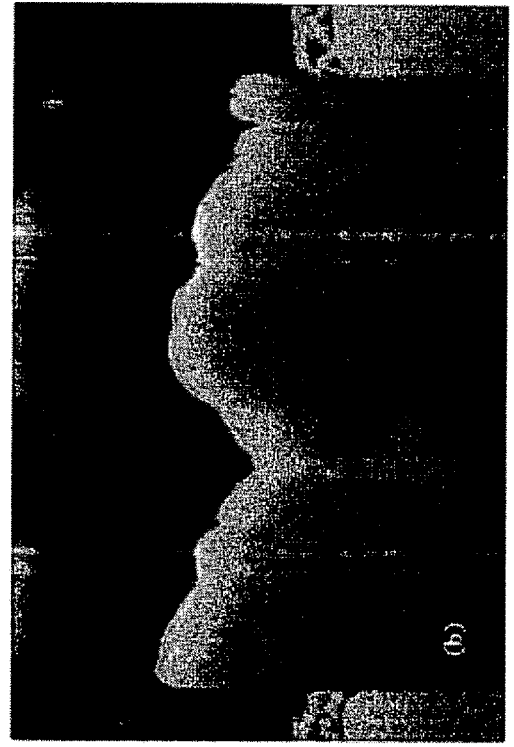
FIG. 3(a) shows a photographic OCT image at the marked B-scan location relating to the vascular tissue of a 10 month old WHHL rabbit.
Figure 3B:
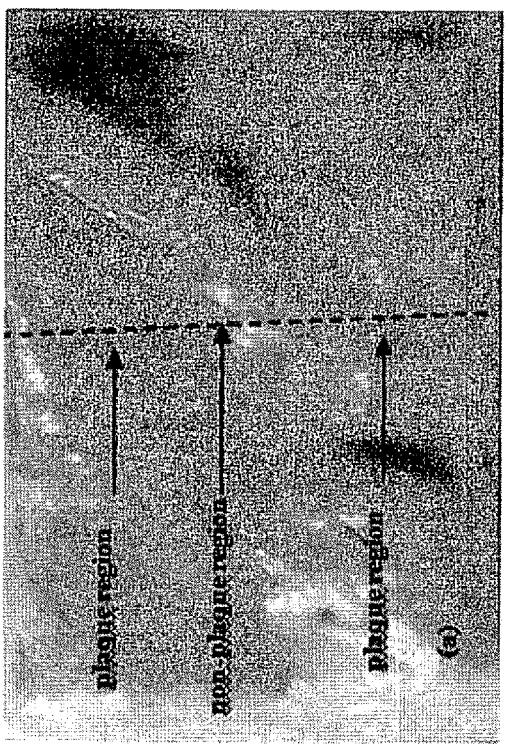
FIG. 3(b) shows a raw OCT image at the marked B-scan location relating to the vascular tissue of a 10 month old WHHL rabbit.
Figure 3E:
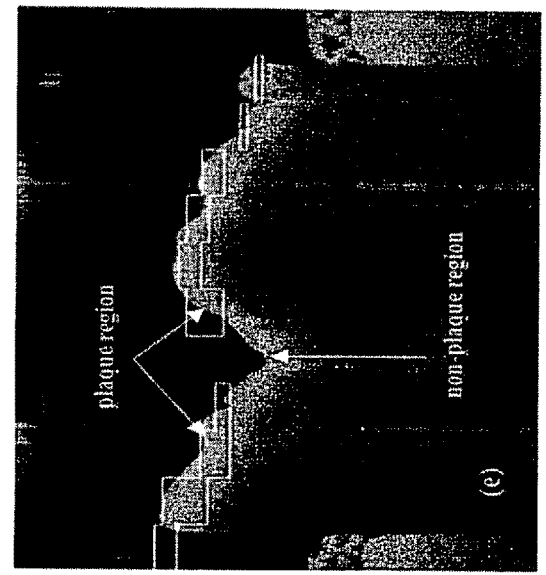
FIG. 3(e) shows the plaque detection results shown on the OCT image with reduced set of 3 textural features relating to the vascular tissue of a 22 month old WHHL rabbit.
Figure 3D:
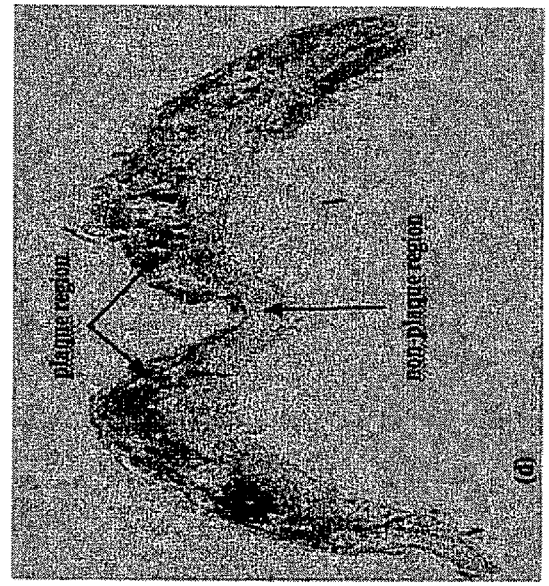
FIG. 3(d) shows the oil red histology image of vascular tissue depicting both plaque and non plaque regions relating to the vascular tissue of a 22 month old WHHL rabbit.
Figure 3C:
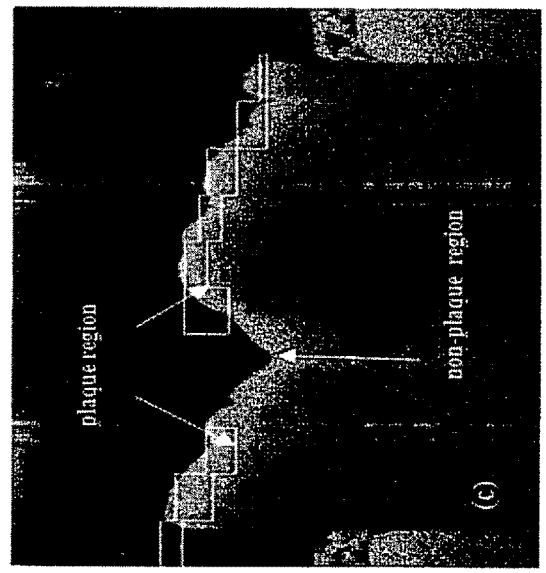
FIG. 3(c) shows plaque detection results as shown on the OCT image with full set of 26 textural features relating to the vascular tissue of a 22 month old WHHL rabbit.

In this work, we obtained vascular tissue samples with atherosclerotic plaque from myocardial infarction prone Watanabe heritable hyperlipidemic rabbits (WHHL rabbits) [16, 17]. Arterial samples were obtained from different locations from three WHHL rabbits aged 10 and 22 months. Arterial segments of tissue starting from the ascending aorta to the external iliac artery were excised from all specimens and subdivided into 20-30 mm long sections. Digital photographs of the luminal surface were taken, and regions of interest were identified prior to measurements. Histology images with oil red O staining were also captured using a Zeiss Axio Observer ZI system (NRC-IBD, Winnipeg, Canada). The oil red O staining emphasizes the lipid content of the tissue, thereby identifying the plaque region. This study was approved by the local animal care committee at the Institute for Biodiagnostics, National Research Council Canada.

The OCT system used in this work is a catheter based intravascular imaging technique that uses near infrared light to create images. [18]. OCT is very similar to ultrasound imaging, only OCT uses light waves instead of sound waves to create images. Because of this, OCT can produce images with resolutions 10 times higher than ultrasound imaging. The wavelength of light in OCT ranges from 1.25 to 1.350 um, which minimizes light wave absorption in water, lipids, and hemoglobin. In OCT, the light from the source is split into two parts: one part is directed toward the arterial wall, and the other part is directed toward a mirror. The reflected signals interfere on a photodetector. The intensity of the interference signal is detected and used to create images. The lateral resolution of the OCT system is within a range of 20-90 mm as opposed to 150-300 mm for IVUS. The axial resolution is 12-18 micron compared to 150-200 micron for IVUS [19]. However, the tissue penetration depth is limited to 1-3 mm in OCT as opposed to 4-8 mm for IVUS. The IVOCT system consists of a catheter, an imaging engine, and a computer. In this work we used a swept-source OCT (SS OCT) using a central wavelength of 1310 nm with a sweep rate and range of 30 khz and 110 nm respectively. Our SS-OCT unit was configured as a Mach-Zehnder interferometer with balanced optical detection.

Texture can be defined as visual patterns composed of spatially repetitive organized structures. Although there is no clear mathematical definition of texture, it can be described using certain qualitative properties of an image. For example, the texture of an image can be referred to as being fine, coarse, smooth, irregular, homogenous, or inhomogeneous, to name just a few. Textural features are those features that can quantify these properties in an image, and an image's textural properties can be characterized by its histogram or its statistical moments. There are several ways to use statistical methods to extract texture features, such as the gray level dependent matrix (SGLDM) method, the grey level difference method (GLDM), the grey level run length method (GLRLM), and the power spectral method (PSM) [20-22]. Although these are all potential methods for extracting textural features, a study comparing these methods has concluded that the SGLDM method is the most powerful texture feature extraction method [23]. Texture features are useful in many applications, such as medical imaging. Image texture has been viewed as being a significant feature of images in medical image analysis, image classification, and automatic image inspection [24, 25]. Our method uses a statistical method to extract texture features of plaque from OCT images. The use of first order statistics is generally insufficient for measuring the structural and textural characteristics of an image because, while first order statistics provide information related to the pixel distribution of an image, they do not provide information about the position or structure these pixels within an image. To extract this information, we used second order statistics where pixels are considered in pairs. Methods of estimating Second-order statistics generate the co-occurrence matrices which are also known as SGLDM [26-28]. The SGLDM matrix provides information on both relative distance and relative orientation among the pixels. In our application of SGLDM we used a distance (d) equal to 1 pixel. We used two different orientations: one in a horizontal direction)($\theta=0°$, and one in a vertical direction (e)=90° which is shown in FIG. 1.

FIG. 1 shows the two (0° and 90°) orientations used to construct SGLDM matrices in our algorithm.

For each combination of d and ( ) a two-dimensional histogram is defined as:

$$0° = P(I(i,j)=I_1, I(i,\pm d,j)=I_2)$$

$$90° = P(I(i,j)=I_1, I(i,j \mp d)=I_2) \quad (1)$$

After using the probabilities of gray level occurrence with respect to pixel position in order to form the SGLDM matrices, we used them to calculate the corresponding Haralick features. Some of these features have a direct interpretation with respect to texture; for example: the Angular second moment feature is the measure of the smoothness of the image; contrast is the measure of local gray level variation within the image; and entropy is the measure of randomness in an image and therefore produces low values for smooth images. However, there are other features which do not possess such a direct interpretation but can still convey texture-related information with high discriminatory power. Table 1 contains all the texture features that we used in our method. In table 1 there is shown all of the Haralick textural features in 0 degrees and 90 degrees with d=1.

An important decision that must be made pertains to choosing the size of the image window over which SGLDM matrices are calculated. Small windows may not have enough pixels to accurately capture the texture of the underlying tissue, while a window that is too large may contain tissues of grossly different textures. We tried different window sizes and found that a window size of 52×52 produced the best resolution for segmentation results.

The scale of the textural features has different dynamic ranges. To ensure that all the features had the same influence on the performance of our method, we normalized the entire textural feature vector. Each textural feature vector was normalized as:

$$\hat{x} = \frac{x - \bar{x}}{\sigma} \qquad (2)$$

Where, x is the raw feature vector, $\bar{x}$ is the mean of all entries of x, and $\sigma$ is the corresponding standard deviation The texture feature selection is made using Genetic algorithm optimization. Our texture feature extraction method generates a set of 26 features. Therefore, the step of feature reduction is critical for optimizing the performance and robustness of our method. Our goal is to reduce the number of features and to select those features that are rich in information with respect to our plaque detection problem. Given this, we used genetic algorithm optimization to reduce the number of texture features to the smallest number possible without sacrificing textural information. Genetic algorithms have been inspired by the biological mechanism of evolution introduced by Darwin [29]. The basic principle of a genetic algorithm is to create the population by randomly selecting combinations of features. Each new population is considered to be an improved solution over the previous one. This procedure takes place for a preselected number of iterations with the best combination of features being found in the last population. The three main operators of a genetic algorithm are the reproduction or selection, crossover, and mutation operators.

We used the fitness function based on Max-Relevance and Min-Redundancy principle [31]. According to this principle, the optimal number of features is selected that satisfies the maximization problem [32]

$$\max_{f_1 \cdots f_{N_n}} \theta \qquad (3)$$

where, $\theta = S - R$ is the objective function $$S = \frac{1}{N} \sum_{i=1}^{N_n} I(X_i; Y) \qquad (4)$$

$$R = \frac{1}{N_n^2} \sum_{i=1}^{N_n} \sum_{j=1}^{N_n} I(X_i; X_j) \qquad (5)$$

In the above equation, S is the mean value of the mutual information $I(X_i;;Y)$ between the features and the output and is the mean value of mutual information between $I(X_i;X_j)$ between the features.

The selection operator selects the population in such a way that better solutions in the current population will have a higher probability of replication. In other words, the better a solution population, the more replicates it will have in the next population. The crossover operator is applied after the application of the reproduction operator. It selects pairs of solutions in a random manner and then splits them at any random position and exchanges their second parts.

To perform crossover operation, each gene of a new individual is selected from one of the parents according to [33], $$T\left(\frac{\exp(gu) - 1}{\exp(u) - 1}\right) \qquad (6)$$

Where, T is the total number of individuals, g is a positive constant value used to tune the selective pressure: the larger the value of g, the faster the algorithm will converge. u is a uniformly distributed random variable.

Our GA algorithm produced the 4 feature set, and we found the common 3 feature set among all the samples which are listed in table 2 which is a list of the selected Haralick texture features set in 0 degrees and 90 degrees with d=1.

In addition the method includes the application of Fuzzy C-means algorithm on reduced feature space.

Clustering is the process of grouping different regions within an image based their different textural properties. Clustering analysis is an unsupervised technique. Unsupervised methods do not require a priori knowledge of samples, i.e., class labels are unknown. Thus the concern in unsupervised methods is to organize the dataset into sensible clusters or groups, which will help in finding the similarities or difference in the dataset. In this work, to perform the clustering, we used Fuzzy C-means clustering algorithm. The Fuzzy C-means method of clustering was developed by Dunn in 1973[30] and was further improved by Bezdek in 1981 [34, 35]. The main advantage of Fuzzy C-means clustering over the standard K-means method is that it is also suited to data which is unevenly distributed around the cluster centroids because it allows data to belong to two or more clusters simultaneously. We therefore used Fuzzy C-means clustering instead of standard K-means clustering. Clustering groups feature vectors into their respective classes.

The algorithm tries to minimize the following objective function:

$$J = \sum_{i=1}^{N} \sum_{j=1}^{C} \mu_{i,j}^k d_{i,j}^2 \qquad (5)$$

Where, J is the objective function, k is the fuzziness constant, and $\mu_{ii}$ is the degree of membership of feature vector xi in the cluster j. N is the total number of data points and C is the number of classes. dij is the Euclidean distance norm between the feature vector and the cluster center.

The first step in Fuzzy C-means clustering is to randomly choose the initial cluster centroids as:

$$C_i = \frac{\sum_{j=1}^{N} \mu_{i,j}^k x_i}{\sum_{j=1}^{N} \mu_{i,j}^k} \qquad (6)$$

Where, Xi is the feature vector, and Ci is the cluster centre.

The second step is to calculate the fuzzy membership criterion and to update the cluster centroid using the membership parameter which is:

$$\mu_{i,j} = \frac{1}{\sum_{m=1}^{C} \left( \frac{\|x_i - c_j\|}{\|x_i - c_m\|} \right)^{\frac{2}{k-1}}} \qquad (7)$$

Where, C is the total number of classes which, in our problem, is 4.

The final step is to repeat these procedures until the algorithm converges.

There are three major parameters of Fuzzy C-means clustering. The first parameter is the number of clusters (C): this is the only parameter that should be known a priori. In our vascular detection problem, there were 4 clusters in total (plaque region, healthy tissue region, OCT degraded signal region and background). The second parameter is the fuzziness Parameter (k): also referred to as the weighting exponent, this parameter influences the fuzziness of the partition clustering and can considerably affect the result of clustering. As k gets closer to I, the partition clustering becomes hard or crisp, similar to conventional K-means clustering. As k–H:t:J (k>I), the partition clustering starts to become fuzzy, allowing for the overlapping of clusters. The standard value for the fuzziness parameter is k=2. The selection of the fuzziness parameter is a complex process, and the accurate selection of the optimal parameter is subjective. The third parameter is the Termination Criterion: the fuzzy c-means algorithm stops the iteration process once the distance between 2 successive iterations is smaller than the termination parameter (r-0.001), or once the algorithm has reached a certain number of iterations. In our problem we used 100 iterations. Also, we assigned the maximum membership index from each group to all the other data points in the cluster. Finally we mapped the clustered regions (plaque region, healthy tissue region, OCT degraded signal region and background back to the original image.

In the plaque detection results, different images of vascular tissue with plaque build-up taken from I O and 22 month old WHHL rabbits are shown in FIGS. 2 and 3. FIG. 2(a) shows a photographic OCT image at the marked B-scan location; FIG. 2(b) shows a raw OCT image at the marked B-scan location; FIG. 2(c) shows plaque detection results as shown on the OCT image with full set of 26 textural features; and FIG. 2 (d) shows the oil red histology image of vascular tissue depicting both plaque and non plaque regions. FIG. 2(e) shows the plaque detection results shown on the OCT image with reduced set of 3 textural features. Similar result is shown in FIG. 3.

The optical coherence tomography (OCT) can be used to perform subsurface imaging of vascular tissue in either static or dynamic mode. In static mode, the OCT probe is fixed, while it optically scans and images the underlying tissue. In dynamic mode, the OCT probe itself is moved over the underlying tissue while imaging it, to cover a much larger imaging field of view.

Dynamic OCT imaging mode is more common in OCT based vascular imaging, where an optical fiber is inserted in a blood vessel and is typically pulled back while imaging (subsurface) the walls of this blood vessel.

The method to detect vascular plaque from OCT images (static case where we are considering a single image) is as follows:
1. Divide the given OCT image into different regular regions where region sizes can vary from many pixels to a single pixel.
2. Calculate different texture features as set forth above defined in for each of the above regions.
3. Use one of many available clustering algorithms to segment the image as now defined by its texture features calculated above into different regions, e.g., healthy tissue, plaque, air, region too deep to image properly, etc. These clustering algorithms can include, K-means, Fuzzy C-means, expectation maximization to fit Gaussian probability mixtures, etc.
4. Transform the segmented image back from its representation using texture features to its space-domain representation.

The reduction of number of features to reduce computations needed for the above algorithm in a onetime step is as follows. Instead of using the full set of 26 Haralick textural features, the present method uses optimization techniques to select a reduced set of features, that is 3 or 4 features, that are enough for successful image segmentation to detect vascular plaque in the given OCT image. The above step is a one-time step performed during the implementation of the algorithm. As well as the possibility to use a genetic algorithm optimization to select a reduced texture feature set, many other optimization techniques can be used.

The method to detect vascular plaque from OCT images (dynamic case where we consider a sequence of overlapping images obtained by moving the OCT probe over the underlying tissue while imaging it) is as follows:
1. We apply the above image segmentation algorithm for the static case to the 1st image of the obtained sequence.
2. Assuming the step size with which the OCT probe moves over an imaged region is small compared to the probe's field of view, i.e., the size of the obtained image, then the obtained (n+1)th image (n=1, 2, 3, . . . ) has many pixels in common with the previous (n)th image.
3. Noting that the clustering algorithms that can be used to segment an image (step 3 of the static case algorithm above) are recursive in nature, in the algorithm (static and dynamic) they segment region pixels (defined by texture features) by assigning them to different image segments over and over again until a steady state solution is reached. A steady state solution means that any further iteration would not change the assignment of any region pixels from their current segment to a different segment.
4. The removal and addition of a relatively small number of region pixels in the n(th) image, compared to the (n−1)th image, only slightly perturbs the steady state solution obtained by the clustering algorithm applied to the (n−1)th image. Therefore we can use this previous steady state solution as a "warm start" to segment the nth image (defined by its texture features). This leads to a dramatic decrease in computational cost compared to starting the segmentation process without such "warm start". This decrease in computational cost allows real-time implementation of this method in the case of dynamic OCT imaging.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:
1. A method for detection of intravascular plaque in OCT images comprising:
Obtaining at least one image of vascular tissue from a vascular component by OCT;
dividing the OCT image into different regular regions;

calculating different texture features for each of the above regions with a reduced set only three or four textural features of the full set of Haralick textural features;

using a clustering algorithm to segment the image as now defined by its texture features calculated above into different regions;

wherein the three or four textural features comprise f1, f2, and f14, wherein f1 represents Angular Second Moment at orientation 0 degrees, f2 represents Inertia at orientation 0 degrees and f14 represents Angular Second Moment at orientation 90 degrees.

2. The method according to claim 1 wherein the reduced set of textural features consists only of f1, f2, and f14.

3. The method according to claim 1 including the step of transforming the segmented image back from its representation using texture features to its space-domain representation.

4. The method according to claim 1 wherein the clustering algorithm comprises Fuzzy C-means.

5. The method according to claim 1 wherein the clustering algorithm comprises K-means.

6. The method according to claim 1 wherein the reduced number of features is selected and arranged so as to decrease the computation time without losing any textural information.

7. The method according to claim 1 including paralleling the algorithms for the reduced number of features so that they are calculated in parallel rather than sequentially so as to further decrease the computation time.

8. The method according to claim 6 wherein the paralleling is done using a CUDA machine.

9. The method according to claim 1 wherein the reduced number of features is selected and arranged so as to reduce the computation time by more than four times.

10. The method according to claim 1 wherein the reduced number of features is selected and arranged for use in real time applications of intravascular plaque detection using OCT images.

11. The method according to claim 10 wherein there is provided a presentation to a technician of a real time image of the plaque detection as the vascular component is scanned using the apparatus.

12. The method according to claim 10 wherein the OCT images are obtained by an optical fiber which is pulled through the vascular component.

13. The method according to claim 1 wherein vascular plaque from OCT images in a dynamic case is detected from a sequence of overlapping images obtained by moving an OCT probe over underlying tissue.

14. The method according to claim 13 wherein the step size with which the OCT probe moves over the tissue is small compared to the probe's field of view so that each obtained image has many pixels in common with a previous image.

* * * * *